US007004944B2

(12) United States Patent
Gause

(10) Patent No.: US 7,004,944 B2
(45) Date of Patent: Feb. 28, 2006

(54) BONE PLATE FASTENER RETAINING MECHANISMS AND METHODS

(75) Inventor: Larry Gause, Memphis, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 409 days.

(21) Appl. No.: 10/196,626

(22) Filed: Jul. 16, 2002

(65) Prior Publication Data

US 2004/0015169 A1     Jan. 22, 2004

(51) Int. Cl.
A61B 17/56 (2006.01)
A61B 17/58 (2006.01)
A61F 2/30 (2006.01)

(52) U.S. Cl. .......................................... 606/69; 606/72

(58) Field of Classification Search .................. 606/61, 606/69, 68, 72, 73, 60; 267/80, 99; 411/102, 411/81, 116, 166
See application file for complete search history.

(56) References Cited

U.S. PATENT DOCUMENTS

| 4,796,612 A | 1/1989 | Reese |
| 5,057,111 A | 10/1991 | Park |
| 5,269,784 A | 12/1993 | Mast |
| 5,881,991 A * | 3/1999 | Bonin ........................ 248/640 |
| 5,951,558 A | 9/1999 | Fiz |
| 6,022,351 A | 2/2000 | Bremer et al. |
| 6,139,550 A | 10/2000 | Michelson |
| 6,228,085 B1 | 5/2001 | Theken et al. |
| 6,261,291 B1 | 7/2001 | Talaber et al. |
| 6,331,179 B1 | 12/2001 | Freid et al. |
| 6,361,537 B1 | 3/2002 | Anderson |
| 6,413,259 B1 | 7/2002 | Lyons et al. |

FOREIGN PATENT DOCUMENTS

EP          1 169 971 A2    1/2002

* cited by examiner

Primary Examiner—Eduardo C. Robert
Assistant Examiner—D. Jacob Davis
(74) Attorney, Agent, or Firm—Krieg DeVault, LLP

(57) ABSTRACT

Retaining mechanisms are attachable to a bone plate to retain one or more bone fasteners in the bone plate. The retaining mechanisms include a retaining element and an attachment element, the attachment element having a distal portion attachable to the bone plate. The retaining element can be distally biased relative to the attachment element. Instruments are engageable to the retaining mechanism to attach the retaining mechanism to the plate.

25 Claims, 7 Drawing Sheets

BONE PLATE FASTENER RETAINING MECHANISMS AND METHODS

BACKGROUND

Bone plates can be engaged to adjacent bony portions of a bone or of a bony segment to stabilize the bone portions. Fasteners can be used to engage the bone plate to the bony portions. To prevent the fasteners from backing out of the plate, various set screw type retaining devices have been developed for engagement to the plate adjacent to or around the bone fasteners. Other retaining devices include an arm integrally formed with the plate and bendable to extend over a fastener in a plate hole. These retaining devices block the fasteners to prevent them from backing out of the plate.

There can be some problems associated with prior retaining devices. For example, in prior retaining devices, the head of one or more of the bone plate fasteners may interfere with the proper positioning and alignment of the retaining device relative to the fasteners. Prior retaining devices may not be positionable in contact with or maintained in contact with one or more of the fasteners if the fasteners move relative to the plate, or if multiple fasteners associated with the retaining device are not at the same position relative to the plate. Also, prior retaining devices can be difficult to handle, install and/or manipulate.

SUMMARY

The present invention includes a retaining mechanism having a retaining element movable relative to the plate when the retaining element is attached to the plate to contact and maintain contact with one or more bone engaging fasteners at a plurality of positions of the bone engaging fastener relative to the plate.

According to one aspect of the invention, there is provided a mechanism for retaining at least one bone engaging fastener relative to a bone plate. The retaining mechanism includes an attachment element attachable to the bone plate and a retaining element coupled to the attachment element. The retaining element is distally biased in contact with the at least one bone engaging fastener when the attachment element is attached to the bone plate. The retaining element is movable proximally relative to the attachment element to contact the at least one bone engaging fastener at a plurality of positions of the at least one bone engaging fastener relative to the bone plate.

According to another aspect of the invention, a mechanism for retaining at least one bone engaging fastener relative to a bone plate is provided. The retaining mechanism includes an attachment element attachable to the bone plate and a retaining element coupled to the attachment element. The retaining element is biased toward the distal portion of the attachment element. When attached to the plate, the retaining element can move against the bias thereof to assume any one of a plurality of positions relative to the attachment element in contact with the at least one bone engaging fastener.

According to a further aspect of the invention, there is provided a mechanism for retaining at least one bone engaging fastener relative to a bone plate. The retaining mechanism includes an attachment element attachable to the bone plate and a retaining element coupled to the attachment element. The retaining element is movable distally and proximally relative to the attachment element to maintain contact with the at least one bone engaging fastener when the attachment element is attached to the bone plate.

According to one aspect of the invention, there is provided a mechanism for retaining at least two bone engaging fasteners relative to in a bone plate. The retaining mechanism includes an attachment element attachable to the bone plate and a retaining element coupled to the attachment element. When the retaining element is attached to the bone plate, the retaining element is pivotally movable relative to the attachment element to contact each of the bone engaging fasteners.

According to another aspect of the invention, there is provided a mechanism for retaining at least one bone engaging fastener relative to a bone plate. The retaining mechanism includes an attachment element having a distal portion attachable to the bone plate and a retaining element extending along a proximal portion of the attachment element. A member extends proximally from the attachment element, and a biasing member extends between the proximally extending member and the retaining element. The biasing member distally biases the retaining element.

According to another aspect of the invention, a mechanism for retaining at least one bone engaging fastener relative to a bone plate is provided. The retaining mechanism includes a portion attachable to the bone plate and a retaining element spring-biased into contact with the at least one bone engaging fastener when the portion is attached to the bone plate.

According to one aspect of the invention, a mechanism for retaining at least one bone engaging fastener relative to a bone plate is provided. The retaining mechanism includes a portion attachable to the bone plate and retaining means contacting the bone engaging fastener. The retaining means is movable relative to the portion attached to the plate to maintain contact with the at least one bone engaging fastener.

According to another aspect of the invention, there is provided a system for stabilizing a bony segment. The system includes a plate having at least one hole therethrough and at least one receptacle adjacent the at least one hole. A bone engaging fastener is positioned in the hole. A retaining mechanism is positioned in the receptacle and includes a retaining element in contact with the bone engaging fastener. The retaining mechanism is biased toward and movable in response to movement of the bone engaging fastener to maintain contact with the bone engaging fastener as the bone engaging fastener moves relative to the bone plate.

According to one aspect of the invention, a system for stabilizing a bony segment is provided that includes a bone plate having at least one pair of adjacent holes therethrough and at least one receptacle adjacent the pair of holes. A bone engaging fastener is positioned in each hole and a retaining mechanism is positioned in the receptacle. The retaining mechanism includes an attachment element having a distal portion attached to the bone plate and a retaining element in contact the bone engaging fasteners positioned in the pair of holes. The retaining element is biased into contact with each of the bone engaging fasteners.

According to another aspect of the invention, a method for securing a bone plate to a spinal column segment is provided. The method includes engaging the bone plate to first and second vertebrae of the spinal column segment with one or more bone engaging fasteners in each of the first and second vertebrae; attaching a retaining mechanism to the bone plate adjacent at least one of the bone engaging fasteners; biasing the retaining mechanism distally into contact with the head of at least one bone engaging fastener; allowing the retaining mechanism to move against the bias of the retaining mechanism while maintaining contact with the at least one bone engaging fastener.

These and other aspects of the invention will also be apparent from the following description.

DESCRIPTION OF THE ILLUSTRATED EMBODIMENTS

Figure 2:
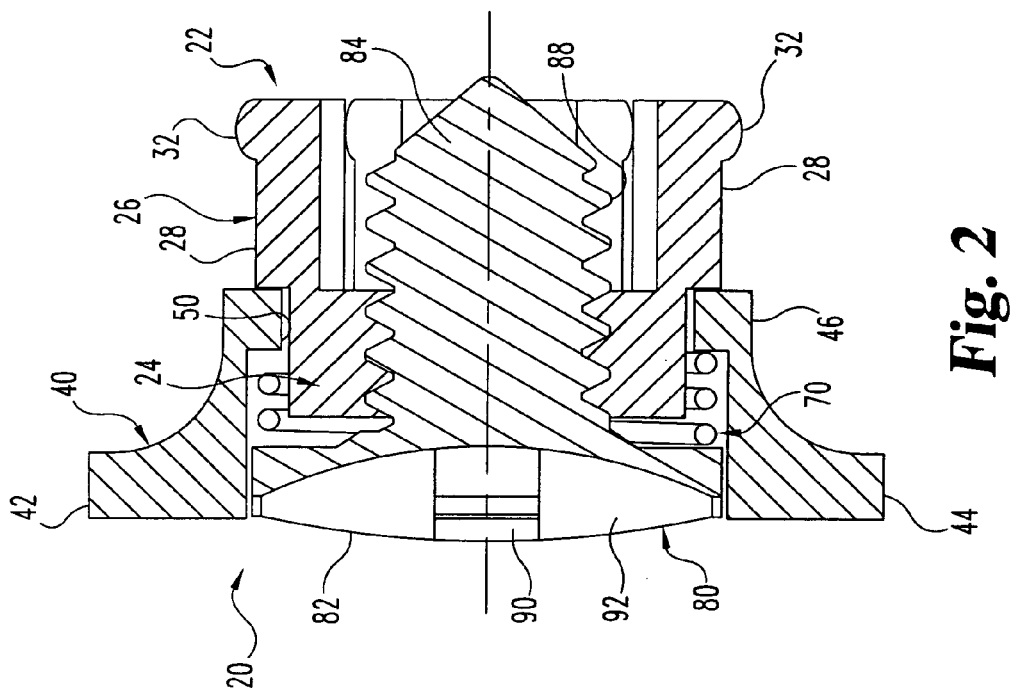
FIG. 2 is a section view through line 2—2 of FIG. 1.

For the purposes of promoting an understanding of the principles of the invention, reference will now be made to the embodiment illustrated in the drawings and specific language will be used to describe the same. It will nevertheless be understood that no limitation of the scope of the invention is thereby intended. Any such alterations and further modifications in the illustrated device and any such further applications of the principles of the invention as illustrated herein are contemplated as would normally occur to one skilled in the art to which the invention relates.

Figure 1:
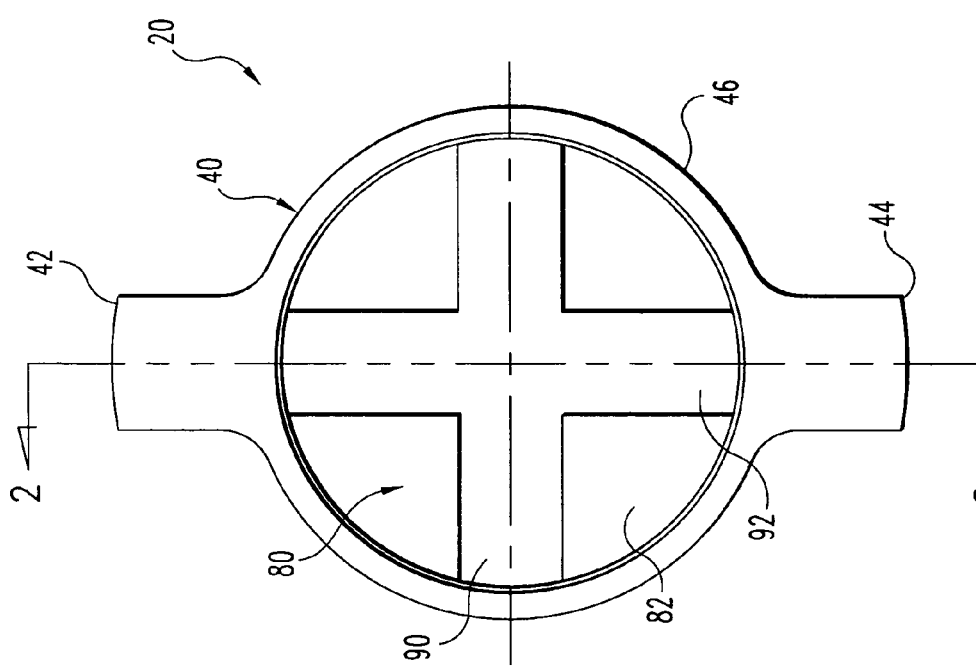
FIG. 1 is a plan view of one embodiment retaining mechanism of the present invention.

In FIGS. 1 and 2 there is shown a retaining mechanism 20 having a retaining element 40 for retaining one or more fasteners relative to a bone plate. Retaining element 40 is coupled to an attachment element 22. Attachment element 22 has a distal portion 26 attachable to the bone plate. Retaining element 40 can be coupled with attachment element 22 and biased distally relative thereto into contact with the one or more bone engaging fasteners. Retaining element 40 is movable distally, proximally and/or by pivoting relative to attachment element 22 to maintain contact with the at least one bone engaging fasteners as the bone engaging fastener moves by pivoting, translating and/or axially moving relative to the plate.

Retaining mechanism 20 can be provided with a member 80 extending proximally from attachment element 22. In the illustrated embodiment, member 80 is in the form of an adjustment member for adjusting the position of retaining element 40 relative to attachment element 22. Other embodiments contemplate that member 80 can be fixed relative to attachment element 22, or integrally formed with attachment element 22. A biasing member 70 extends between member 80 and retaining element 40 to bias retaining element 40 distally and allowing proximal and/or pivotal movement of retaining element 40 relative to attachment element 22. Retaining element 40 can be provided with extensions 42, 44 extending laterally therefrom to contact the heads of adjacent bone engaging fasteners.

In the illustrated embodiment, biasing member 70 is a coil spring. Other forms for biasing member 70 are also contemplated, including one or more struts, cylinders, bushings, or spacers. Biasing member 70 can be made from any resiliently deformable material, such as, for example, metal and metal alloys, plastic material, elastomeric material, spring steel, stainless steel, shape memory material, and combinations thereof.

Retaining element 40 and attachment element 22 can be made from metal or metal alloy, such as titanium or stainless steel, and also plastic material, ceramic material, or other suitable biocompatible material.

Figure 4:
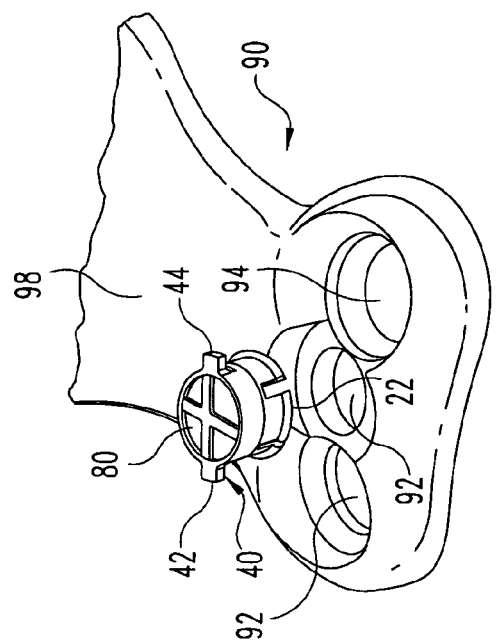
FIG. 4 is an enlarged perspective view of one end of the plate and retaining mechanism of FIG. 3.
Figure 3:
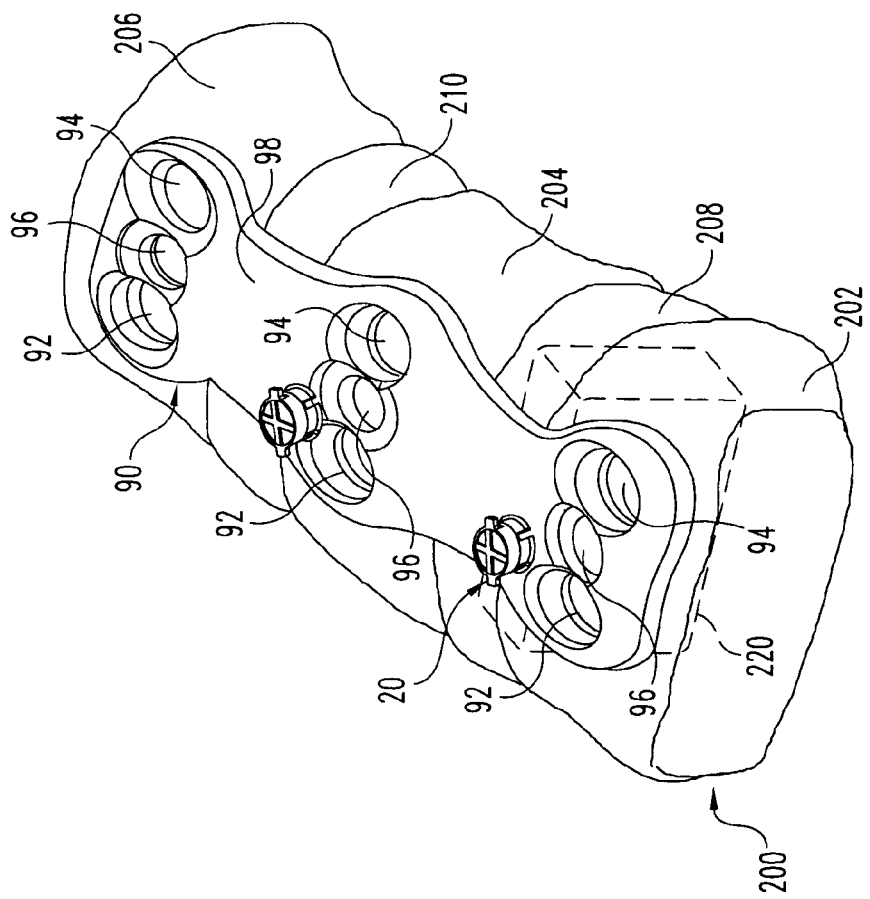
FIG. 3 is a perspective view of one embodiment of a plate along a bony segment and a pair of retaining mechanisms of FIGS. 1 and 2 positioned adjacent thereto before attachment to the plate.
Figure 5:
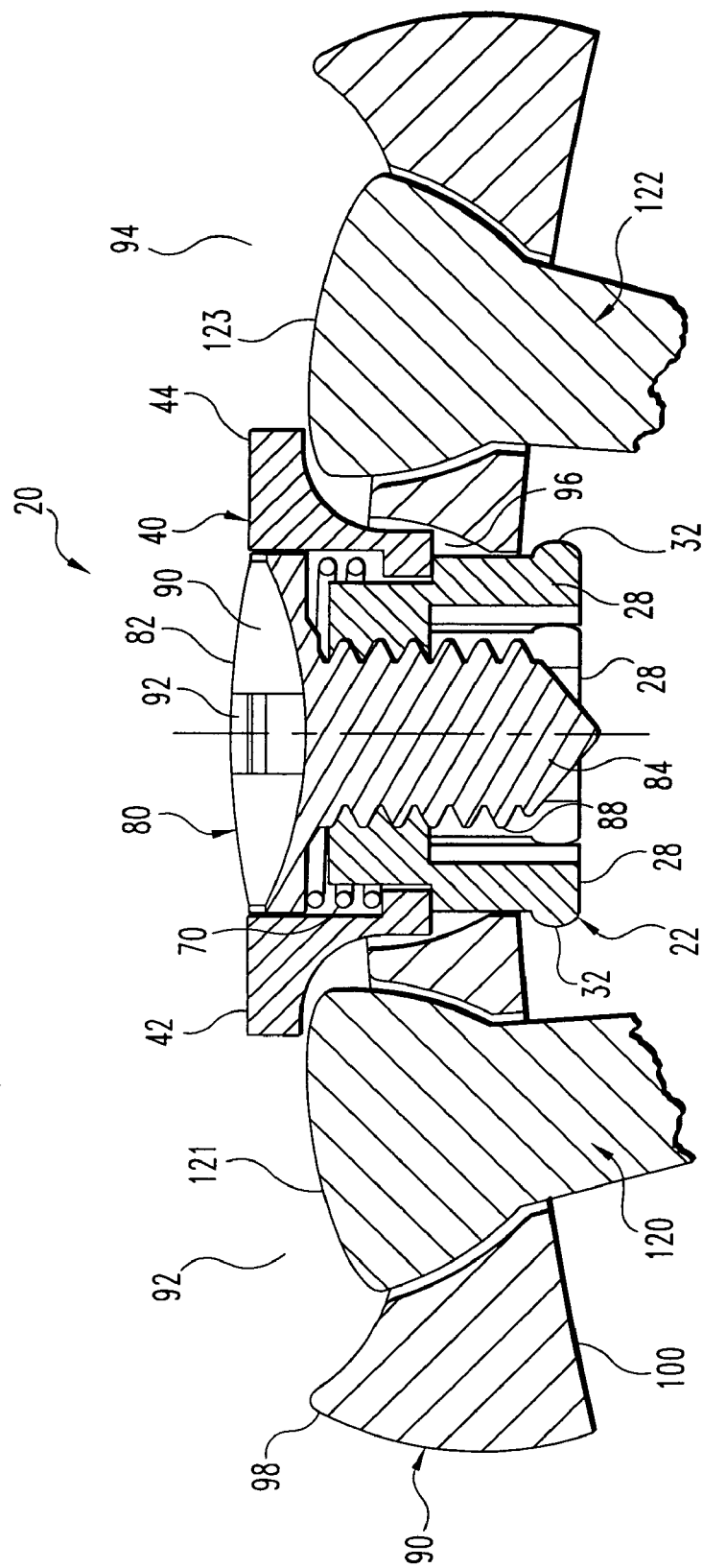
FIG. 5 is a section view through one embodiment plate and bone engaging fasteners with the retaining mechanism of FIGS. 1 and 2 attached to the plate.

In use, retaining mechanism 20 is attachable to a bone plate, such as bone plate 90 shown in FIGS. 3–5. Bone plate 90 includes adjacent holes 92, 94 therethrough between a proximal surface 98 and a distal surface 100. Holes 92, 94 are sized to receive bone engaging fasteners 120, 122 to secure plate 90 to bone structure under plate 90. Holes 90, 92 can be circular or elongated along the axis of the plate. Bone engaging fasteners 120, 122 can be any bone engaging fastener, such as a screw, anchor, bolt, or other fastener capable of securing plate 90 to bone structure. Receptacles 96 can be provided between adjacent ones of the holes 92, 94 to receive retaining mechanism 20. Retaining mechanism 20 is configured to contact the heads 121, 123 of fasteners 120, 122 when fasteners 120, 122 are positioned in holes 92, 94 and retaining mechanism 20 is positioned in receptacle 96 to prevent and/or limit the backout of fasteners 120, 122 relative to plate 90.

Retaining element 40 is biased distally toward the heads 121, 123 of fasteners 120, 122 and can move proximally relative attachment element 22 and plate 90. The biasing force supplied by biasing member 70 maintains contact between extensions 42, 44 of retaining element 40 and heads 121, 123 of fasteners 120, 122. Biasing member 70 allows retaining element 40 to pivot and/or move proximally relative to attachment element 22 and plate 90. Extensions 42, 44 can thus be placed in and maintained in contact with fasteners 120, 122 even if the heads 121, 123 are not at the same position relative to upper surface 98 of plate 90.

Retaining mechanism 20 can be used with bone plates and fasteners in which pivoting and/or translation of the fasteners relative to the plate is desirable while preventing or limiting the back out of the fasteners from the plate. Retaining mechanism 20 can also be used with bone plates and fasteners in which the fasteners are fixed relative to the plate to prevent or limit the back out of the fixed fasteners from the plate. The same retaining mechanism 20, or multiple retaining mechanisms 20, can also be employed with any one or combination of fixed, pivotal, and translatable fasteners in the same bone plate.

By way of illustration and not limitation, various examples regarding the contact between retaining mechanism 20 and fasteners 120, 122 will be provided. In use, fastener 120 may move proximally by way of backing out from, translating and/or pivoting in hole 92, while fastener 94 remains in its inserted position in hole 94. Retaining element 40 can pivot relative to attachment element 22 so that extension 42 moves proximally or distally with fastener 120 while extension 44 remains in contact with fastener 122. The proximal movement of fastener 120 can be stopped or limited when, for example, biasing member 70 is fully compressed adjacent extension 42. Fastener 122 can also move proximally until biasing member 70 is fully compressed adjacent extension 44.

In another example, one or both of the fasteners 120, 122 may move distally in holes 92, 94 as a result of, for example, translation or pivoting movement of the fasteners relative to plate 90. Biasing member 70 biases retaining element 40 distally, maintaining contact of the extensions 42, 44 with the head of the adjacent fastener 120, 122. The distal movement of retaining element 40 can be stopped or limited by, for example, contact between retaining element 40 and attachment element 22, or contact with retaining element 40 and plate 90, or the unbiased length of biasing member 70. It is contemplated that the retaining mechanism can be configured relative to plate 90 and fasteners 90, 92 so that extensions 42, 44 can contact the head of the adjacent fastener in any position of the head of the fastener in its respective hole.

In the illustrated embodiment, plate 90 is an anterior cervical plate having three nodes therealong and a pair of holes 92, 94 at each node. Receptacle 96 is positioned between each of the hole pairs 90, 92, and is adapted to receive retaining mechanism 20 therein so that extensions 42, 44 of retaining element 40 can contact the heads of bone fasteners 120, 122 in respective ones of the holes 92, 94. Receptacle 96 can be sized so that the proximal extension of member 80 and retaining element 40 from proximal surface 98 is minimized or eliminated. Further, receptacle 96 can be in communication with or overlap the proximal portion of holes 92, 94 so that extensions 42, 44 can extend into holes 92, 94 to contact the head of the bone engaging fastener positioned therein.

It is contemplated that retaining mechanism 20 can have application with other shaped and sized plates for the anterior cervical spine, and with spinal plates for other regions of the spine, including the thoracic, lumbar, and/or sacral portions of the spine. Retaining mechanism 20 can be employed with spinal plates adapted for attachment to other locations of the spine, including the anterior, antero-lateral, lateral, and posterior portions of the spine. It is further contemplated that retaining mechanism 20 can have application in bone plates other than those used in spinal surgery. It is also contemplated that a receptacle in the bone plate for receiving retaining mechanism 20 can be positioned adjacent only one of the fastener holes, adjacent a pair of the fastener holes, or adjacent three or more fastener holes. It is further contemplated that a plate could be provided one or more fastener holes without any receptacle adjacent thereto.

In some applications, it is contemplated that the bone plate will be used to stabilize a spinal column segment 200. For example, in FIG. 3 there is shown a cervical spinal column segment 200 with vertebrae 202, 204 and 206. Disc space 208 is located between vertebrae 202, 204, and disc space 210 is located between vertebrae 204, 206. An implant, such as implant 220 in disc space 208, can be positioned in one or both of the spinal disc spaces 208, 210. Plate 90 can then be attached to two or more of the vertebrae to stabilize spinal column segment 200.

It is contemplated that implant 220 could be a bone graft, interbody fusion device, artificial disc device, or other interbody implant. Such implants can be made from bone material, man-made material, or combinations thereof. In procedures where fusion of the adjacent vertebrae is desired, bone growth material and bone growth facilitators could be provided to facilitate such fusion. Any suitable osteogenetic material or composition is contemplated for placement within or around implant 220. Such osteogenic material includes, for example, autograft, allograft, xenograft, demineralized bone, synthetic and natural bone graft substitutes, such as bioceramics and polymers, and osteoinductive factors. A separate carrier to hold the materials in the disc space or in the implant can also be used. These carriers can include collagen-based carriers, bioceramic materials, such as BIO-GLASS®, hydroxyapatite and calcium phosphate compositions. The carrier material can be provided in the form of a sponge, a block, folded sheet, putty, paste, graft material or other suitable form. Moreover, the osteogenetic compositions can comprise an effective amount of a bone morphogenetic protein, transforming growth factor $\beta 1$, insulin-like growth factor 1, platelet-derived growth factor, fibroblast growth factor, LIM mineralization protein (LMP), and combinations thereof or other therapeutic or infection resistant agent, held within a suitable carrier material.

Figure 7:
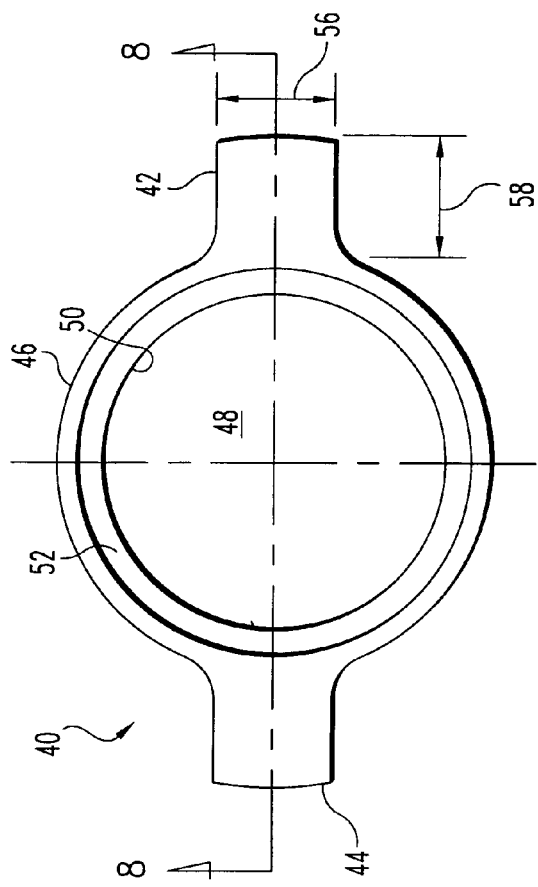
FIG. 7 is an enlarged plan view of the retaining element of FIG. 6.
Figure 8:
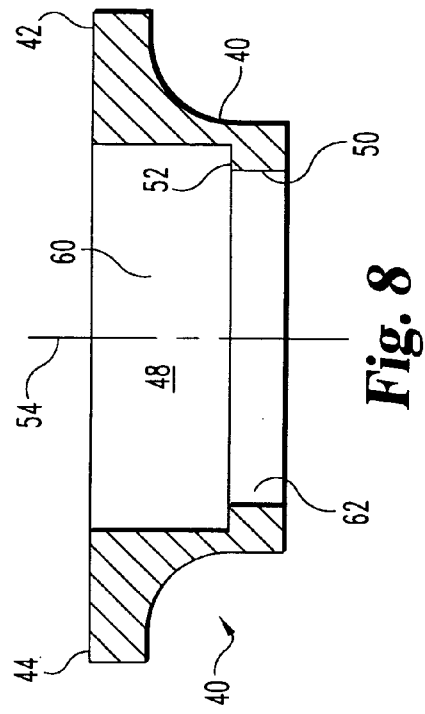
FIG. 8 is a section view through line 8—8 of FIG. 7.
Figure 6:
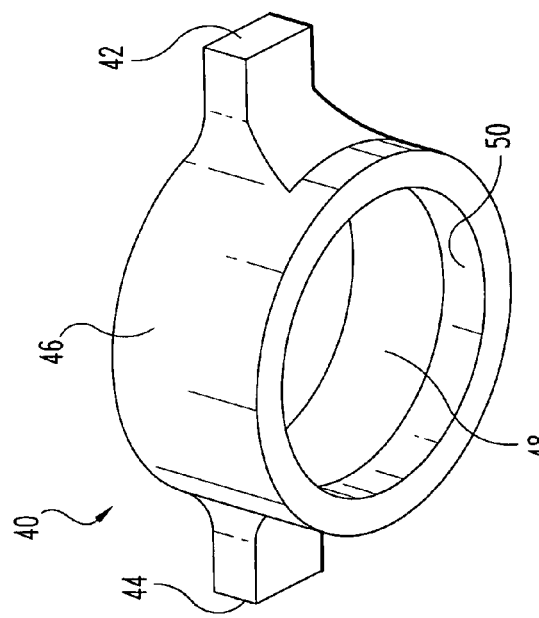
FIG. 6 is a perspective view of a retaining element comprising a portion of the retaining mechanism of FIGS. 1 and 2.

Further details of retaining mechanism 20 are provided in FIGS. 6–14. Referring to FIGS. 6–8, retaining element 40 includes first extension 42 and opposite second extension 44. Each of the extensions 42, 44 extend laterally from a body 46 that extends around a central passage 48. Retaining element 40 includes a radially inwardly extending flange 50 that forms a lip 52 around passage 48. Lip 52 divides passage 48 into a proximal portion 60 and a distal portion 62.

Each of the extensions 42, 44 has a width 56 along body 46 and a length 58 extending from body 46. Length 58 is sufficient to extend over at least a portion of a head of a fastener adjacent thereto. Extensions 42, 44 can be sized to cover all or a portion of the head of the bone engaging fastener. In the embodiment of FIGS. 1, 2 and 6–8, two extensions are shown offset 180 degrees from one another about body 46. It is further contemplated that other offsets for the extensions and/or other numbers of extensions could be provided for retaining element 40.

Figure 10:
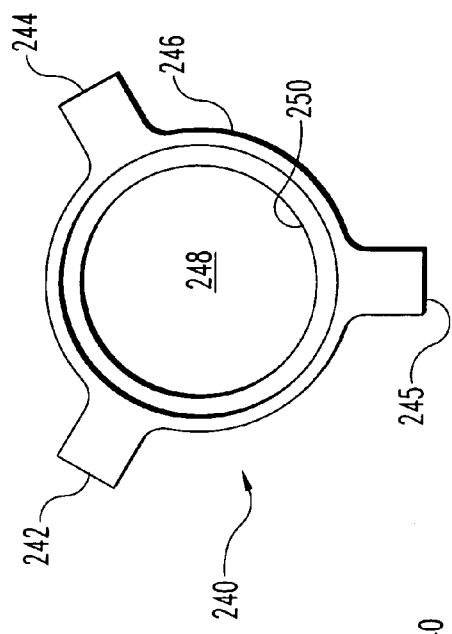
FIG. 10 is a plan view of another embodiment retaining element.
Figure 11:
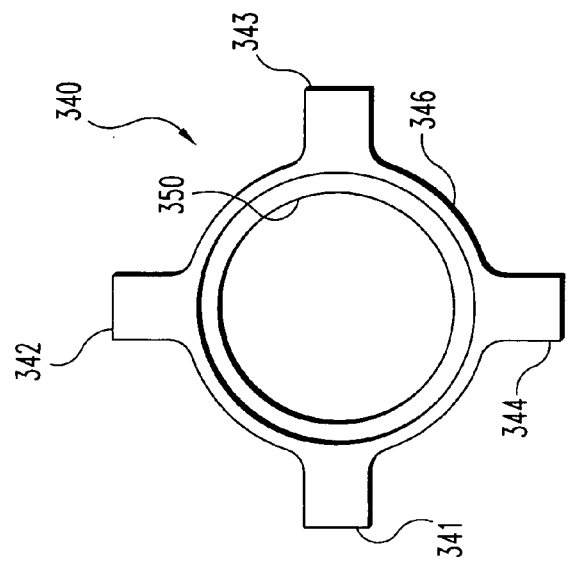
FIG. 11 is a plan view of another embodiment retaining element.
Figure 9:
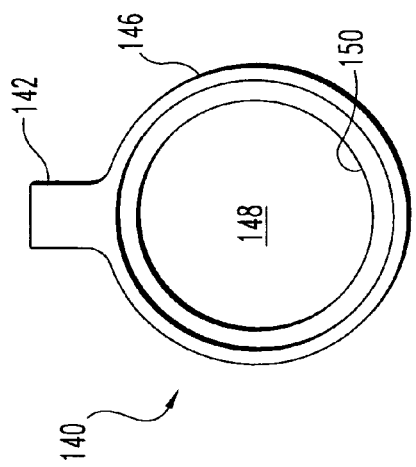
FIG. 9 is a plan view of another embodiment retaining element.

For example, in FIG. 9 there is retaining element 140 including a body 146 extending around central passage 148 and a flange 150 extends radially inwardly toward passage 148. Body 146 includes one extension 142 extending therefrom. In FIG. 10 there is retaining element 240 having a body 246 extending around a central passage 248 and a flange 250 extends radially inwardly toward passage 248. Body 246 includes three extensions 242, 244, 245 extending therefrom. Extensions 242, 244, 245 can be spaced at 120 degree intervals about body 146, although other intervals, including non-equal intervals, are contemplated. In FIG. 11 there is retaining element 340 having a body 346 extending around central passage 348 and a flange 350 extends radially inwardly toward passage 348. Body 346 includes four extensions 341, 342, 343, 344 extending therefrom. Extensions 341, 342, 343, 344 can be spaced at 90 degree intervals about body 346, although other intervals, including non-equal intervals, are contemplated.

Figure 13:
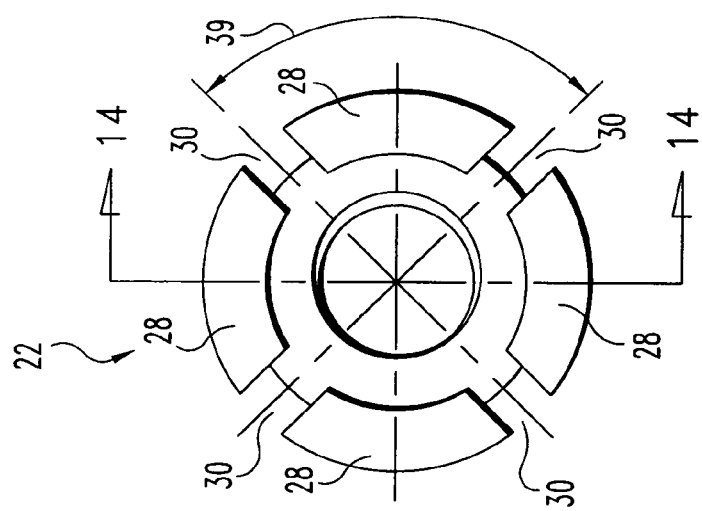
FIG. 13 is a plan view looking at the bottom of the attachment element of FIG. 12.
Figure 14:
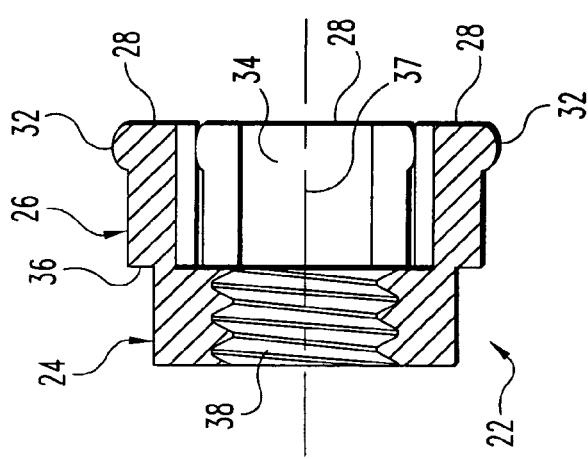
FIG. 14 is a section view through line 14—14 of FIG. 13.
Figure 12:
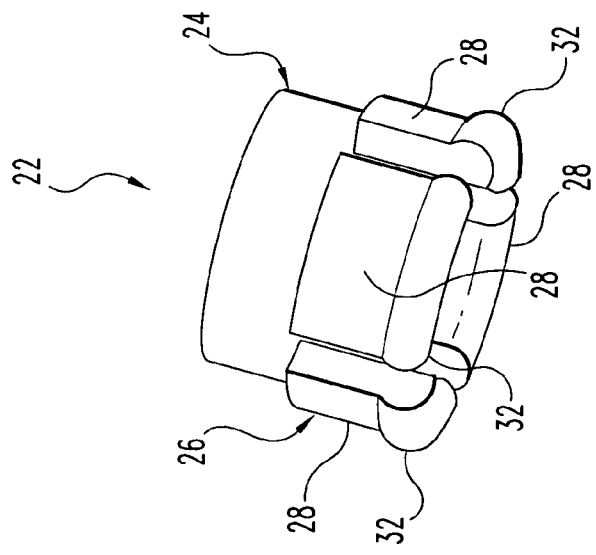
FIG. 12 is a perspective view of an attachment element comprising a portion of the retaining mechanism of FIGS. 1 and 2.

Referring to FIGS. 12–14, attachment element 22 includes a proximal portion 24 and a distal portion 26.

Proximal portion 24 can be provided with a passage 38 sized to receive member 80 therein. A lip 36 extends radially outwardly between proximal portion 24 and distal portion 26. Distal portion 26 can include a number of attachment members 28 positioned thereabout and configured to engage the bone plate. Attachment members 28 each include a protrusion 30 extending therefrom in a radially outward direction.

In the illustrated embodiment, attachment members 28 can be spaced from one another by gaps 30, allowing attachment members 28 to flex radially inwardly and return outwardly to attach retaining mechanism 20 to the bone plate. In the illustrated embodiment, four attachment members 28 are provided and spaced from one another by four gaps 30 between adjacent ones of the attachment members 28. Gaps 30 are centrally spaced at an angle 39 from another. In the illustrated embodiment angle 39 is about 90 degrees. Other embodiments contemplated fewer or more attachment members 28 and gaps 30. For example, one continuous attachment member 28 could be provided. In another example, one attachment member is provided with a single gap. In further examples, there could be provided two attachment members and two gaps spaced therebetween, three attachment members and three gaps spaced therebetween, five attachment members and five gaps spaced therebetween, and so on.

When retaining mechanism 20 is attached to the bone plate, protrusions 32 ride along the sides of the receptacle, such as receptacle 96, and deflect retaining members 28 inwardly during insertion. As shown in FIG. 5, when protrusions 32 are positioned through receptacle 96, retaining members 28 return toward their pre-insertion configuration, and protrusions 32 engage distal surface 100 of plate 90, attaching retaining mechanism 20 thereto.

Other forms for attachment element 22 are also contemplated. For example, distal portion 26 could be threaded to engage a threaded receptacle in the bone plate. It is further contemplated that attachment element 22 could be configured to frictionally engage the receptacle, welded or fused with the bone plate, or otherwise captured in or attached to the bone plate.

With retaining mechanism 20 assembled, proximal portion 24 can be positioned in lower portion 62 of passage 48 such that a central axis 54 of retaining element 40 is generally aligned with a central axis 37 of attachment element 22. Flange 50 can rest on lip 36 of attachment element 22. Biasing member 70 can be placed about proximal portion 24 and into contact with lip 52 of flange 50 and a head 82 of member 80. In the illustrated embodiment, member 80 includes a head 82 with tool recesses 90, 92.

It is contemplated that, retaining element 40 could be non-rotatable relative to attachment element 22 and/or member 80. It is also contemplated that retaining element 40 could be rotatable about attachment element 22 and/or member 80 so that the positioning of extensions 42, 44 can be adjusted, or that all or a portion of retaining mechanism 20 can be rotated relative to the plate. For example, the bone plate could be configured to allow the retaining mechanism to be pre-attached to the plate before engagement of the plate to the bony segment. Retaining element 40 could be rotated to move extensions 42, 44 away from the plate holes for insertion of the bone engaging fasteners. When the fasteners are inserted, retaining mechanism 20 or retaining element 40 could be rotated relative to the plate so that extensions 42, 44 contact the bone engaging fasteners.

It is further contemplated that, as shown in FIGS. 3 and 4, retaining element 40 could be substantially non-rotatable relative to the bone plate when attached thereto due to interference between the extensions 42, 44 and the sides of receptacle 96. In such cases, the retaining mechanism 20 is top-loaded for attachment to the plate to place extensions 42, 44 directly into contact with the bone engaging fasteners after placement of the bone engaging fasteners in the plate holes.

Member 80 can be configured to adjust the range of distal and proximal movement of retaining element 40 relative to attachment element 22 and the bone plate. In the illustrated embodiment, member 80 includes shaft 84 having thread pattern 88 therealong. Before or after attachment of retaining mechanism 20 to the bone plate, member 80 can be threadingly advanced distally in bore 38 toward attachment element 22 to compress biasing member 70 between head 82 and flange 50. Head 82 can be received in proximal portion 60 of passage 48 to minimize or eliminate the proximal extension of member 80 from retaining element 40. Member 80 can also be threaded proximally in bore 38 to reduce the compression of biasing member 70, and to provide a greater range of proximal movement for retaining element 40. Maintaining some proximal movement capability for retaining element 40 allows the fasteners to pivot or translate in the plate holes, if the plate and/or fasteners are so configured, while extensions 42, 44 maintain contact therewith.

When attachment element 22 is attached to the plate, biasing member 70 biases retaining element 40 and thus extensions 42, 44 into contact with the head of the adjacent bone engaging fastener, even if the heads are at differing proximal or mismatched positions relative to the plate. As member 80 is threadingly advanced distally into attachment element 22, biasing member 70 is compressed between retaining element 40 and head 82. When biasing member 70 is fully compressed adjacent one or both of the extensions 42, 44, or when head 82 contacts the proximal end of proximal portion 24, member 80 cannot be advanced further into bore 38. The surgeon is thus provided a tactile indication that contact is made with extensions 42, 44 and the adjacent bone engaging fastener. Compressing biasing element 70 reduces or, if fully compressed, prevents proximal movement of retaining element 40, thus limiting or preventing the proximal movement of the bone engaging fasteners in contact therewith.

As discussed above, it is also contemplated that member 80 can be provided without adjustment capability, and is fixed or formed with attachment element 22. It is contemplated that biasing member 70 can provide sufficient distal biasing force on retaining element 40 so that extensions 42, 44 contact the adjacent bone engaging fastener. The distal positioning of extensions 42 44 can be limited by contact between the distal end of retaining element 40 and lip 36. Lip 36 can be positioned relative to the plate so that extensions 42, 44 can contact the bone engaging fasteners in their distal-most position relative to the plate, ensuring that retaining element 40 can contact the adjacent bone engaging fasteners when attached to the plate.

Figure 15:
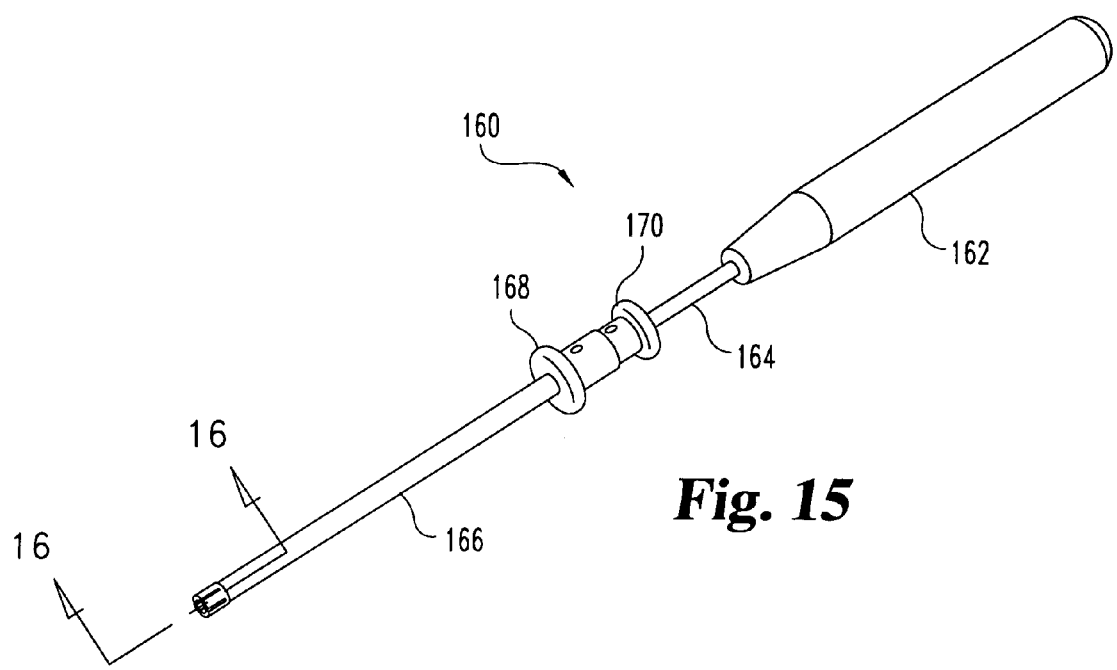
FIG. 15 is a perspective view of one embodiment attachment instrument for attaching the retaining mechanism to a plate.
Figure 16:
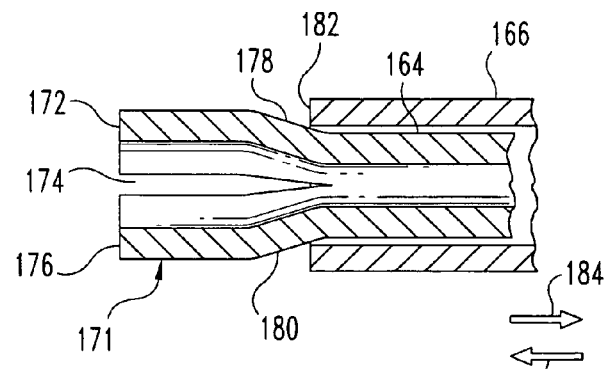
FIG. 16 is a section view of a distal end portion of the attachment instrument of FIG. 15 through line 16—16 of FIG. 15.

Referring to FIGS. 15 and 16, there is shown an insertion instrument 160 for inserting retaining mechanism 20. Insertion instrument 160 includes a gripping member 162 extending distally therefrom. An actuating member 166 is positioned about gripping member 164. Actuating member 166 includes a first coupling member 168 at a proximal end thereof that is engageable with a second coupling member 170 of gripping member 164. Coupling members 168, 170 can be threadingly or slidingly engaged with one another so that actuating member 166 can be moved distally and proximally relative to gripping member 164.

As shown in FIG. 16, a distal end 171 of gripping member 164 includes a pair of gripping fingers 172, 176 spaced by a receptacle 174 on each side thereof (only one shown.) Receptacle 174 can extend proximally a sufficient distance to impart at least some flexibility to gripping fingers 172, 176 so that they can be moved away from and/or toward one another. Extensions 42, 44 of retaining element 40 can be received in receptacles 174 so that gripping fingers 172, 176 can be positioned about body 46 of retaining element 40. To grip retaining element 40, actuating member 166 is advanced distally along gripping member 164 so that distal end 182 of actuating member 166 moves along ramped portions 178, 180 of gripping fingers 172, 176, respectively, forcing them toward one another and into engagement with body 46.

With gripping member 164 engaged to retaining element 40, retaining mechanism 20 can be held on the distal end of instrument 160 for positioning retaining element 20 in the corresponding receptacle in the plate. The inserted retaining mechanism can be released from insertion instrument 160 be moving actuating member 166 proximally, allowing gripping fingers 172, 176 to move away from one another and release retaining element 40.

Other insertion instruments for releasably gripping retaining mechanism 20 are also contemplated. For example, the actuating member and gripping member could be movable relative to one another by a linkage mechanism, trigger mechanism, sliding movement, threaded movement or other coupling arrangement therebetween. The distal end of the insertion instrument could be configured to frictionally, magnetically, adhesively, grippingly or otherwise configured to hold either or both of the retaining element and adjustment member of the retaining mechanism.

While the invention has been illustrated and described in detail in the drawings and foregoing description, the same is to be considered as illustrative and not restrictive in character. All changes and modifications that come within the spirit of the invention are desired to be protected.

What is claimed is:

1. A mechanism for retaining at least one bone engaging fastener relative to a bone plate, comprising:
    an attachment element having a distal portion attachable to the bone plate;
    a retaining element extending along a proximal portion of said attachment element;
    a member extending proximally from said attachment element; and
    a biasing member extending between said member and said retaining element biasing said retaining element distally.

2. The mechanism of claim 1, wherein said retaining element includes:
    a passage extending therethrough receiving said proximal portion of said attachment element; and
    a flange adjacent a distal end of said retaining element extending radially inwardly toward said passage, said biasing member in contact with said flange.

3. The mechanism of claim 1, wherein said biasing member is a spring.

4. The mechanism of claim 1, wherein said member is threadingly engaged to said attachment element.

5. A mechanism for retaining at least one bone engaging fastener relative to a bone plate, comprising:
    an attachment element attachable to the bone plate;
    a retaining element coupled to said attachment element, wherein said retaining element is distally biased to contact the at least one bone engaging fastener when said attachment element is attached to the bone plate, said retaining element being movable proximally relative to said attachment element to contact the at least one bone engaging fastener at a plurality of positions of the at least one bone engaging fastener relative to the bone plate, wherein:
    said attachment element includes a proximal portion and a distal portion attachable to the bone plate, said proximal portion being received in a passage of said retaining element;
    said distal portion includes a number of attachment members therearound; and
    each of said number of attachment members is radially inwardly deflectable for insertion of said distal portion through a receptacle in the bone plate.

6. The mechanism of claim 5, wherein each of said attachment members includes a protrusion extending radially outwardly therefrom, each of said protrusions engaging a distal surface of the plate when said attachment element is attached to the bone plate.

7. A mechanism for retaining at least one bone engaging fastener relative to a bone plate, comprising:
    an attachment element attachable to the bone plate;
    a retaining element coupled to said attachment element, wherein said retaining element is distally biased to contact the at least one bone engaging fastener when said attachment element is attached to the bone plate, said retaining element being movable proximally relative to said attachment element to contact the at least one bone engaging fastener at a plurality of positions of the at least one bone engaging fastener relative to the bone plate, wherein:
    said attachment element includes a proximal portion and a distal portion attachable to the bone plate, said proximal portion being received in a passage of said retaining element;
    said retaining element includes a flange adjacent a distal end thereof extending radially inwardly toward said passage;
    an adjustment member extending through said passage of said retaining element and coupled to said attachment element; and
    a biasing member extending between and in contact with said flange and said adjustment member.

8. A mechanism for retaining at least one bone en a in fastener relative to a bone plate, comprising:
    an attachment element attachable to the bone plate; and
    a retaining element coupled to said attachment element, wherein said retaining element is distally biased to contact the at least one bone engaging fastener when said attachment element is attached to the bone plate, said retaining element being movable proximally relative to said attachment element to contact the at least one bone engaging fastener at a plurality of positions of the at least one bone engaging fastener relative to the bone plate, wherein said attachment element includes a proximal portion and a distal portion attachable to the bone plate, said proximal portion being received in a passage of said retaining element and said attachment element includes a lip extending radially outwardly between said proximal portion and said distal portion of said attachment element, said lip contactable with a distal end of said retaining element to limit distal movement of said retaining element relative to said attachment element.

9. The mechanism of claim 8, further comprising an adjustment member coupled to said attachment element.

10. The mechanism of claim 9, further comprising a biasing member extending between said adjustment member and said retaining element distally biasing said retaining element.

11. The mechanism of claim 10, wherein said biasing member is a spring.

12. The mechanism of claim 9, wherein said adjustment member is threadingly engageable with an internally threaded bore of said attachment element.

13. The mechanism of claim 8, wherein said retaining element includes at least one extension extending laterally therefrom in contact with the at least one bone engaging fastener.

14. The mechanism of claim 8, wherein said retaining element includes a pair of opposite lateral extensions.

15. The mechanism of claim 8, wherein said distal portion includes a number of attachment members therearound.

16. The mechanism of claim 8, wherein said retaining element includes a flange adjacent a distal end thereof extending radially inwardly toward said passage.

17. The mechanism of claim 8, wherein said retaining element is pivotal relative to said attachment element.

18. A mechanism for retaining at least one bone engaging fastener relative to a bone plate, comprising:
an attachment element having a distal portion attachable to the bone plate; and
a retaining element coupled to said attachment element, said retaining element being biased toward said distal portion of said attachment element and movable against said bias in contact with the at least one bone engaging fastener to assume any one of a plurality of positions relative to said attachment element when said distal portion is attached to the bone plate;
a member extending proximally from said attachment element; and
a biasing member extending between said member and said retaining element distally biasing said retaining element.

19. The mechanism of claim 18, wherein said retaining element includes at least one extension extending laterally therefrom for contacting the at least one bone engaging fastener.

20. A mechanism for retaining at least one bone engaging fastener relative to a bone plate, comprising:
an attachment element having a distal portion attachable to the bone plate; and
a retaining element coupled to said attachment element, said retaining element being biased toward said distal portion of said attachment element and movable against said bias in contact with the at least one bone engaging fastener to assume any one of a plurality of positions relative to said attachment element when said distal portion is attached to the bone plate, wherein said retaining element includes:
a passage extending therethrough receiving a proximal portion of said attachment element; and
a flange adjacent a distal end thereof extending radially inwardly toward said passage.

21. The mechanism of claim 20, further comprising a member extending proximally from said attachment element.

22. The mechanism of claim 20, further comprising:
an adjustment member coupled to said attachment element and extending through said passage of said retaining element; and
a biasing member extending between and in contact with said flange and said adjustment member.

23. The mechanism of claim 22, wherein said adjustment member is movable relative to said attachment element to compress said biasing member.

24. A mechanism for retaining at least two bone engaging fasteners relative to a bone plate, comprising:
an attachment element attachable to the bone plate;
a retaining element coupled to said attachment element, said retaining element being movable relative to said attachment element when said attachment element is attached to the bone plate to contact each of the at least two bone engaging fasteners at mismatched positions of the at least two bone engaging fasteners relative to the plate, wherein said retaining element includes a passage extending therethrough receiving a proximal portion of said attachment element and a flange adjacent a distal end thereof extending radially inwardly toward said passage;
an adjustment member extending through said passage of said retaining element and coupled to said attachment element; and
a biasing member extending between and in contact with said flange and said adjustment member.

25. The mechanism of claim 24, wherein said retaining element includes at least two extensions extending laterally therefrom for contacting respective ones of the at least two bone engaging fasteners.

* * * * *

UNITED STATES PATENT AND TRADEMARK OFFICE
CERTIFICATE OF CORRECTION

| | | |
|---|---|---|
| PATENT NO. | : 7,004,944 B2 | Page 1 of 1 |
| APPLICATION NO. | : 10/196626 | |
| DATED | : February 28, 2006 | |
| INVENTOR(S) | : Larry Gause | |

It is certified that error appears in the above-identified patent and that said Letters Patent is hereby corrected as shown below:

In claim 8, line 1, replace "en a in" with --engaging--.

Signed and Sealed this

Eighteenth Day of September, 2007

JON W. DUDAS
*Director of the United States Patent and Trademark Office*